(12) United States Patent
Masinaei et al.

(10) Patent No.: US 7,498,040 B2
(45) Date of Patent: Mar. 3, 2009

(54) COMPOSITIONS FOR REPAIR OF DEFECTS IN OSSEOUS TISSUES, AND METHODS OF MAKING THE SAME

(75) Inventors: Leila Masinaei, Norfolk, VA (US); Lloyd Wolfinbarger, Jr., Norfolk, VA (US)

(73) Assignee: LifeNet Health, Virginia Beach, VA (US)

( * ) Notice: Subject to any disclaimer, the term of this patent is extended or adjusted under 35 U.S.C. 154(b) by 107 days.

(21) Appl. No.: 11/247,229

(22) Filed: Oct. 12, 2005

(65) Prior Publication Data

US 2007/0082057 A1 Apr. 12, 2007

(51) Int. Cl.
*A61K 9/00* (2006.01)
*C12N 5/02* (2006.01)

(52) U.S. Cl. ...................................... 424/400; 424/422

(58) Field of Classification Search ................ 424/400, 424/422; 435/325, 372
See application file for complete search history.

(56) References Cited

U.S. PATENT DOCUMENTS

| | | | |
|---|---|---|---|
| 5,531,791 A | 7/1996 | Wolfinbarger, Jr. | |
| 5,674,292 A | 10/1997 | Tucker et al. | |
| 5,948,428 A | 9/1999 | Lee et al. | |
| 6,013,856 A | 1/2000 | Tucker et al. | |
| 6,028,242 A | 2/2000 | Tucker et al. | |
| 6,180,606 B1 | 1/2001 | Chen et al. | |
| 6,372,257 B1 | 4/2002 | Marchosky | |
| 6,458,375 B1 | 10/2002 | Gertzman et al. | |
| 6,461,630 B1 | 10/2002 | Tucker et al. | |
| 6,504,079 B2 | 1/2003 | Tucker et al. | |
| 6,576,249 B1 | 6/2003 | Gendler et al. | |
| 6,679,918 B1 | 1/2004 | Benedict et al. | |
| 6,933,326 B1 | 8/2005 | Griffey et al. | |
| 2004/0059364 A1* | 3/2004 | Gaskins et al. | 606/180 |

* cited by examiner

*Primary Examiner*—Ruth A Davis
(74) *Attorney, Agent, or Firm*—Morgan Lewis & Bockius LLP

(57) ABSTRACT

Tissue repair compositions, particularly bone repair compositions, containing demineralized bone fragments and homogenized connective tissues, and methods for making the same. The compositions can be used in the form of an injectable gel, an injectable paste, a paste, a putty, or a rehydratable freeze-dried form.

75 Claims, No Drawings

COMPOSITIONS FOR REPAIR OF DEFECTS IN OSSEOUS TISSUES, AND METHODS OF MAKING THE SAME

BACKGROUND OF THE INVENTION

The ability to promote tissue regrowth in vivo can facilitate wound healing and post-surgical recovery of patients who have suffered tissue damage or destruction. A variety of methods and compositions have been used to repair or regenerate bone tissue in vivo. The need for such methods and compositions is readily apparent, when considering that in 1999, approximately 500,000 bone graft procedures were performed in the United States alone. Ideal bone graft materials for use in such procedures possess characteristics necessary to new bone growth, namely osteoconductivity and osteoinductivity.

Osteoconductivity refers to a graft's ability to support the attachment of new osteoblasts and osteoprogenitor cells. The osteoconductive components of a graft provide an interconnected structure through which new cells can migrate and new blood vessels can form. Osteoinductivity refers to the ability of a graft to induce nondifferentiated stem cells. or osteoprogenitor cells to differentiate into osteoblasts.

In 1998, 9 of 10 bone graft procedures performed in the United States involved the use of either autograft or allograft bone tissue. Despite the benefits of autografts and allografts, the limitations of each have necessitated the pursuit of alternative graft materials. Using basic criteria necessary to a successful graft (e.g., osteoconduction and osteoinduction), investigators have developed several bone graft substitutes. These can contain a variety of materials, including natural and synthetic polymers, ceramics, and composites; and in some instances, production of bone graft substitutes can involve biotechnological strategies (i.e., factor- and/or cell-based strategies).

Osteoinductive substances found in some bone graft substitutes are demineralized bone particles and/or powder. Contained in the extracellular matrix of bone tissue is a full cocktail of bone growth factors, proteins, and other bioactive materials necessary for osteoinduction and, ultimately, successful bone healing. To capitalize on this cocktail of proteins, bone tissue can be demineralized, leaving the osteoinductive agents in the demineralized bone matrix (DBM). Such osteoinductive DBM can be incorporated into a number of different bone graft substitutes.

While a number of different materials thought to enhance osteoconductivity (i.e., purified or partially purified polymers) have been used in DBM bone graft substitutes; new, more easily prepared, osteoconductive/structural materials for combining with DBM to produce a bone graft substitute are desirable.

SUMMARY OF THE INVENTION

Certain embodiments of the present invention are directed to tissue repair compositions and methods of preparing the same. Some tissue repair compositions of the present invention may be in the form of a fluid injectable gel, a fluid injectable paste, a putty, or a rehydratable freeze-dried paste. Some embodiments of the present invention may be used in clinical applications, such as spinal procedures, orthopedic procedures and dental procedures.

Some embodiments of the present invention are directed to tissue repair compositions having a plurality of demineralized bone fragments and a carrier. The carrier comprises homogenized connective tissue. The demineralized bone fragments may be demineralized bone particles or demineralized bone fibers, in certain embodiments. In some embodiments, demineralized bone fragments may be derived from allogenic cortical bone or xenogenic cortical bone. Demineralized bone fragments may, in certain embodiments, have less than about 8 wt % residual calcium. The tissue repair composition may comprise between about 5 wt % and about 90 wt % demineralized bone fragments, in some embodiments. In certain embodiments, the connective tissue that has been homogenized may be fascia, skin, tendon, ligament, pericardium, articular cartilage, or mixtures thereof. Homogenized connective tissue used in some embodiments of the present invention may be comprised of tissue fragments having an average diameter of less than about 50 microns.

Certain embodiments are directed to methods of preparing a tissue repair composition. The methods comprise combining a plurality of demineralized bone fragments and a carrier having homogenized connective tissue. Certain methods further comprise at least one of a bone fragmentation step, a connective tissue fragmentation step, a bone demineralization step, a selecting of demineralized bone fragments of a particular size range step, a freeze-drying step, a rehydrating step, a heating step, a connective tissue homogenization step, a packaging step, and a sterilization step.

Certain embodiments of the present invention are directed to prosthetic devices comprising, an implantable prosthetic device, and a coating directly adjacent to at least a portion of a surface of the implantable prosthetic device. The coating comprises at least one tissue repair composition comprising a plurality of demineralized bone fragments and a homogenized connective tissue.

Some embodiments of the present invention are directed to a method of coating a prosthetic device comprising, providing an implantable prosthetic device, and applying at least one tissue repair composition to at least a portion of a surface of the implantable prosthetic device. The tissue repair composition is as described above.

DETAILED DESCRIPTION

In the present application, the term "connective tissue" refers to mesodermally derived tissue that may be more or less specialized, and that is, at least in part, made up of fibers. Most of the connective tissues contemplated in the present invention are less specialized tissues that are rich in extracellular matrix (i.e., collagen, proteoglycan, among others), and that surround other more highly ordered tissues and organs. A relatively, more specialized tissue contemplated in the present invention is cartilage. Varieties of connective tissue that may be used in the present invention include: loose; adipose; dense, regular or irregular; white fibrous; elastic; and cartilage. Connective tissue may be classified according to concentration of fibers as loose (areolar) and dense, the latter having more abundant fibers than the former. Connective tissues may be obtained from vertebrates. In some embodiments, the tissues may have human, bovine, equine, porcine, ovine, caprine, or piscene origins, among others. Connective tissues may also be the product of biotechnological methods (i.e., production of tissue engineered connective tissues using cell culture methods).

Specific examples of connective tissues that may be used in certain embodiments of the present invention include, at least, fascia, skin, tendons, ligaments, pericardium, and articular cartilage. Different types of fascia that may be used in certain embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. "Crudely fragmented connective tissue" refers to connective tissue that has been sliced, ground, carved, chipped, chopped, minced, cut, dissected, rent, ripped, sectioned, snipped, diced, shaved, comminuted, or trimmed into fragments having an average diameter greater than about 50 microns and less than about 0.5 cm (i.e., having cut dimensions of approximately 0.5×0.5 cm), and thickness appropriate to the tissue being crudely fragmented. In some embodiments, the crude fragments may not be of uniform size.

"Homogenized connective tissue" or "connective tissue homogenate" contains connective tissue that has been reduced to particles that are uniformly small and evenly distributed. Homogenized connective tissue may optionally include at least one of water, aqueous solutions, or water miscible polar organic solvents, in addition to the particles. The homogenized connective tissues used in methods of the present invention include particles having an average diameter of less than about 50 microns. In some embodiments, the homogenized connective tissue may be prepared by shear-induced shredding of a composition comprising connective tissue, and optionally, at least one of water, an aqueous solution and a water miscible polar organic solvent. A conventional blender may be used in preparing the homogenized connective tissue, in certain embodiments.

"Osseous tissue" is meant to refer to bone tissue, tissue resembling bone, and tissue capable of forming bone. The term "bone" or "bone tissue" is intended for the purposes of the invention to refer to autograft bone, allograft bone, and xenograft bone. Such bone includes any bone from any source, including: bone from a living human donor, bone from a human cadaveric donor, and bone from an animal. The bone may include cortical bone and/or cancellous bone and/or cortico-cancellous bone. The term "bone fragment," as used in the present application refers to ground bone, pulverized bone, bone cubes, bone chips, bone strips, bone particles, and bone fibers. Bone fragments may be "bone particles" or "bone fibers," in some embodiments of the present invention. "Bone particle" refers to a piece of bone having an average diameter of between about 125 microns and about 4 mm. "Bone fiber" refers to a filament or thread of bone having an average thickness of between about 0.1 mm and about 1.4 mm and an average width of between about 0.3 mm and about 2.5 mm. Fibers can be of varying lengths. In certain embodiments, a bone fiber can have an average length of between about 1.0 mm and about 100 mm. In certain embodiments, bone fiber contains lamellae in the shape of threads or filaments having a median length to median thickness ratio of about 10:1.

"Demineralized bone," as used in the present application refers to bone having less than about 8 wt % residual calcium. Demineralization involves treating the surface of a bone tissue to remove a surface layer of its inorganic mineral hydroxyapatite material leaving the mechanical properties of the organic phase of the bone constructs substantially unchanged. The level of demineralization of a bone tissue is defined by the amount (wt %) of residual calcium found in the demineralized bone. In some embodiments, the demineralized bone may contain physiologically active levels of growth and differentiation factors (i.e., bone morphogenetic proteins (BMPs)).

In the present application, the term "gel" refers to a jelly-like, thick, soft, partly liquid substance. A gel of the present invention may be extruded through at least a 13 gauge syringe needle. "Paste," as used in the present application refers to a soft, moist, substance having a consistency between a liquid and a solid. A paste of the present invention is less solid than a putty and more solid that a gel, and in some embodiments may be injectable.

"Putty" refers to a dough-like/clay-like tissue repair composition of the present invention. During application the substance may be beaten or kneaded to the consistency of dough, and molded into a shape closely approximating that of the implant site.

"Injectable" refers to the ability of certain tissue repair compositions of the present invention to be introduced at an implant site under pressure (as by introduction using a syringe). An injectable composition of the present invention may, for example, be introduced between elements or into a confined space in vivo (i.e., between pieces of bone or into the interface between a prosthetic device and bone, among others).

"Syringe" refers to any device that may be used to inject or withdraw flowable tissue repair compositions of the present invention, including certain gels and pastes, among others.

"Flowable" refers to the characteristic of a composition that permits it to be made to fit closely by following the contours of a site. Flowable compositions may be fluid, malleable, plastic, and/or pliable.

"Allogenic tissue" refers to a tissue from a donor that is implanted into a recipient of the same species. Allograft tissue is widely used in orthopedic, neuro-, maxillofacial, podiatric, and dental surgery. The tissue is valuable because it is strong, biointegrates in time with the recipient patient's tissue and may be shaped to fit the specific surgical defect. Contrasted to most synthetic absorbable or nonabsorbable polymers or metals, allograft tissue is biocompatible and integrates with the surrounding tissues. Allograft bone occurs in two basic forms: cancellous and cortical.

"Xenogenic tissue" refers to a tissue from one species that is implanted into a recipient of another species.

"Cortical bone," as used in the present application, refers to the compact bone of the shaft of a bone that surrounds the medullary cavity. Cortical bone is a highly dense structure made up of triple helix strands of collagen fiber, reinforced with hydroxyapatite. The cortical bone is a compound structure and is the primary load bearing component of long bones in the human body. The hydroxyapatite component is responsible for the high compressive strength of the bone while the collagen fiber component contributes in part to torsional and tensile strength.

Trabecular bone is of similar composition to cortical bone and is the primary structural component of "cancellous bone" and refers to adult bone consisting of mineralized regularly ordered parallel collagen fibers organized differently than in the lamellar bone of the shaft of adult long bones. Cancellous bone is generally found in the end of long bones surrounded by cortical bone. Cancellous bone has spicules that form a latticework, with interstices filled with bone marrow. It may also be referred to as a trabecular bone, or spongy bone.

"Aseptic" as a term can be applied to both products and processes and is generally applied to the control or reduction in microbial bioburden. Tissues processed "aseptically" are tissues processed using sterile instruments, and special environmental surroundings (including for example "clean room technologies"). Aseptic tissues make reference to tissues that are "culture negative," where culture negative makes reference to the use of representative pieces of tissue that have been or will be processed for an assessment of the presence of microorganisms. The level of sensitivity of the microbiological test method(s), and hence a better definition of "culture negative," is generally predetermined by assessing for interference in the detection of such microorganisms (sometimes referred to as bacteriostasis and fungistasis, B&F, testing).

"Sterile" makes reference to a definition such as contained in the Code of Federal Regulations (21 CFR) where the probability of a culturable microorganism being present on a processed sample is equal to or less than 1 in one million, i.e., a Sterility Assurance Level, or SAL, of $1 \times 10^{-6}$.

An "osseous defect" is generally defined by one skilled in the art as being an imperfection or void in an osseous tissue, which is of sufficient physical dimensions as to not heal spontaneously. Hence, the use of materials generally referred to as "bone void fillers" are utilized clinically to aid or improve healing of the osseous defect. Certain compositions of the present invention can be used as bone void fillers. Osseous defects may include: fractures, cracks, and osteosarcomas (bone cancer lesions), among others. Bone void fillers may be used to fill a gap between a prosthetic device and bone; between pieces of bone; and between two different prosthetic devices. For example, a bone void filler can be used to fill the space between a hip replacement and a bore in a bone into which the hip replacement has been inserted Certain embodiments of the present invention are directed to tissue repair compositions comprising a plurality of demineralized bone fragments and a carrier. The carrier includes at least one homogenized connective tissue. In some embodiments, the tissue repair composition may be safely used in repairing damaged osseous tissues (e.g., damaged bone) in an implant patient. The tissue repair composition may, in some embodiments, be biocompatible, osteoinductive, and/or osteoconductive, such that it may ultimately be remodeled to a mineralized, hard tissue at the application site in vivo. In certain embodiments, the tissue repair compositions may further include at least one of water, an aqueous solution, a water miscible polar organic solvent, and other components described below. The tissue repair composition may include materials that improve handling or functional characteristics post-implantation. In some embodiments, bone and connective tissue may be obtained from the same donor source (i.e., a single human cadaver donor). The formulation of the inventive tissue repair composition may be highly reproducible. In certain embodiments, the tissue repair composition may be aseptic or sterile.

The composition may be in the form of a gel, a paste, a putty, or a freeze-dried substance that can be rehydrated to produce a paste or a putty. In some embodiments, the gel or paste may be injectable, and the gel or paste may be extrudable through a syringe and/or a syringe having at least a 13 gauge tube/needle coupled thereto. Certain gels and pastes may be used for accurate delivery of the tissue repair composition into narrow junctions with minimal surgical damage to surrounding tissue at the implant site. Some of the tissue repair compositions of the present invention may be moldable. Tissue repair compositions of the present invention may be cast into a shaped form, in certain embodiments.

In some embodiments, each of (a) the demineralized bone fragments and (b) the homogenized connective tissue of the inventive composition may include materials derived from allogenic or xenogenic sources. In certain embodiments, bone and connective tissues obtained from vertebrate species, for example human, bovine, porcine, ovine, caprine, and piscene sources may be used to prepare demineralized bone fragments and carrier. The plurality of demineralized bone fragments may include more than one type of bone tissue (e.g., cancellous, cortical, or cortico-cancellous bone), and the homogenized connective tissue may include more than one type of connective tissue (i.e., fascia and tendon). The plurality of demineralized bone fragments may include bone from a single donor source, or from multiple donor sources, and the homogenized connective tissue may also include tissue from a single donor source, or from multiple donor sources.

For preparation of the tissue repair compositions of the present invention, the carrier comprising the connective tissue homogenate and the demineralized bone fragments are combined together. In some embodiments, the tissue repair composition may include between about 5 wt % and about 90 wt %; between about 20 wt % and about 80 wt %; and between about 30 wt % and about 50 wt % demineralized bone fragments. Certain tissue compositions of the present invention that are in the form of a gel or paste may include between about 20 wt % and about 30 wt % demineralized bone fragments, while certain compositions of the present invention that are in the form of a putty may include between about 25 wt % and about 40 wt % of the demineralized bone fragments. In some embodiments, the tissue repair composition may be in the form of a freeze-dried product that may be rehydrated to produce a paste or a putty, which may include between about 35 wt % and about 50 wt % demineralized bone fragments.

In certain embodiments, the tissue repair composition may include demineralized bone fragments having less than about 8 wt % or less than about 4 wt % residual calcium. The tissue repair composition may include demineralized bone fragments having between about 0.5 wt % and about 4 wt % residual calcium, in some embodiments. In certain embodiments, the tissue repair composition may include between about 0.25 wt % and about 80 wt % or about 0.5 wt % and about 5 wt % of the connective tissue homogenate. The amount of homogenized connective tissue used in a tissue repair composition may be used to adjust the viscosity and gelation characteristics of the composition.

The plurality of demineralized bone fragments may include at least one of demineralized bone particles and demineralized bone fibers, in some embodiments. The demineralized bone fragments may include materials derived from allogenic or xenogenic sources. The demineralized bone fragments may be derived from cortical bone or cancellous bone. In certain embodiments, the plurality of demineralized bone fragments includes at least one of demineralized allogenic cortical bone particles, demineralized xenogenic cortical bone particles, demineralized allogenic cancellous bone particles, and demineralized xenogenic cancellous bone particles.

Certain tissue repair compositions of the present invention may include demineralized bone particles. Demineralized bone particles may be prepared from cleaned and disinfected bone fragments that have been freeze-dried and ground/fractured into bone particles. Bone particles may be selected by, for example, using sieving devices (i.e., mesh sieves) commercially available to obtain particles within a desired size range. Such demineralized bone particles may have an average diameter of between about 125 microns and about 4 mm; between about 710 microns and about 2 mm; between about 125 microns and about 500 microns; between about 125 microns and about 850 microns; or between about 250 microns and about 710 microns. Certain embodiments of the present invention may include demineralized bone powder that is commercially available. For example, a suitable demineralized bone powder that is widely and reliably available is produced by LifeNet, Virginia Beach, Va.

Some tissue repair compositions of the present invention may include demineralized bone fibers. Fiber bone may be produced as described in U.S. patent application Ser. No. 10/606,208, published as publication number 2004/0059364, which is hereby incorporated by reference in its entirety. In certain embodiments, the demineralized bone fibers may have an average thickness of between about 0.1 mm and about 0.3 mm and an average width of between about 0.3 mm and about 1.0 mm. The length of the fibers may vary. Any demineralization processes known in the art, may be used to prepare demineralized bone fragments. Such processes are described in U.S. Pat. Nos. 6,830,763; 6,534,095; 6,305,379; 6,189,537; 5,531,791; and 5,275,954. In some embodiments, the demineralization process begins by producing bone particles having an average diameter size range of between about 1 mm and about 2 mm or bone fibers having an average dimension of 0.1 mm to 0.3 mm thick and an average width of about 0.3 mm to about 1 mm. The fragments may then be treated by such processes as are described in U.S. Pat. Nos. 5,556,379; 5,797,871; 5,820,581; 5,976,104; 5,977,034; 5,977,432; and 6,024,735, which are hereby incorporated by reference in their entirety. If the bone to be processed into fragments has not been previously cleaned and disinfected, they may be cleaned and disinfected by the use of detergents, hydrogen peroxides, antibiotics, and alcohols to affect a removal of associated tissues such as bone marrow and cellular elements. Following a cleaning and disinfection, these fragments (i.e., particles and fibers) may be demineralized by exposure to dilute hydrochloric acid, such as are known in the art, to affect a removal/reduction of the mineral component of the bone fragments (i.e., particles and fibers). Such additional processing may, in some instances, inactivate potential viral contamination (i.e., HIV and hepatitis viruses, among others).

In certain embodiments in which demineralized bone fragments are to be used later, they may be conveniently stored by freeze-drying, which may maintain the activity of their bioactive components (i.e., BMPs, among others). If the demineralized bone fragments are to be used later, in some embodiments, the acidic demineralization solution may be removed from the bone using aqueous or polar (miscible with water) organic solutions, for example deionized/distilled endotoxin-free water, saline solutions, acetone, alcohol(s), and dimethylsulfoxide, in order to minimize elevated levels of salts in the freeze-dried bone.

Tissue repair compositions of the present invention include a carrier having a homogenized connective tissue. In some embodiments, the carrier and/or connective tissue homogenate may include a biocompatible liquefied form of connective tissue (i.e., liquefied human connective tissue) that when combined with demineralized bone fragments, has suitable viscosity so as to be injectable through large gauge applicators, while largely remaining at the implant site. The carrier may promote cellular infiltration and retain the demineralized bone fragments at the site of application, without being cytotoxic. The carrier may promote such cellular infiltration by providing a molecular matrix for cell migration. In some embodiments, the carrier/connective tissue homogenate may be freeze-dried.

In some embodiments, the homogenized connective tissue may be prepared from allogenic or xenogenic tissue. Such connective tissue may be obtained from a human donor or an animal (i.e., bovine donor, porcine donor, etc.). Connective tissue may be obtained relatively economically. Varieties of connective tissue that may be used in certain embodiments of the present invention include: areolar or loose; adipose; dense, regular or irregular; white fibrous; elastic; and cartilage. Specific examples of connective tissues that may be used in certain embodiments of the present invention include, at least: fascia, skin, tendons, ligaments, pericardium, and articular cartilage. Different types of fascia that may be used in some embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. For practical reasons of availability during procurement and amount of fascia available, fascia lata from the anterior portion of the upper leg may be used in certain embodiments. Homogenized connective tissue may be prepared by methods involving, cleaning and disinfecting connective tissue, and removing extraneous tissues associated with the connective tissue. Connective tissues may be cut into small pieces to produce crudely fragmented connective tissue, and optionally triturated and washed with distilled/deionized endotoxin-free water and/or an aqueous solution (i.e., isotonic saline, among others). In processing, multiple "washes" may be affected using volumes of aqueous solution that are 10 times the approximated volume of the tissue being processed, in some embodiments. It would be obvious to one skilled in the art that the use of three such processing steps would affect an approximate 1:1000 dilution of associated solubilizable elements rendering the tissue essentially free from such solubilizable elements Connective tissue may be treated and homogenized at temperatures sufficient to produce a flowable homogenized connective tissue, in certain embodiments. The homogenized connective tissue may include connective tissue that has been reduced to particles that are uniformly small and evenly distributed. Homogenized connective tissue and/or the carrier may optionally include at least one of water, aqueous solutions (i.e., isotonic saline), and water miscible polar organic solvents in addition to the connective tissue particles. In some aspects, the homogenized connective tissue may include gelatin. The homogenized connective tissues used in methods of the present invention may include particles having an average diameter of less than about 50 microns, less than about 20 microns, or less than about 50 microns and greater than about 5 microns. In some embodiments, the homogenized connective tissue and optionally, at least one of a water miscible polar organic solvent, water and an aqueous solution, may be prepared by shear-induced shredding of connective tissue. A conventional blender may be used in preparing the homogenized connective tissue, in certain embodiments.

In some embodiments of the present invention, connective tissue homogenate and/or the carrier will retain large and small molecular weight macromolecules, including hyaluronate which is known to play a role in cell migration (Toole, B. P. and Trelstad, R. L. 1971, Develop. Biol. 26:28-35; Docherty, R. et al., 1989, J. Cell. Sci. 92:263-270) and has been implicated in facilitating fibril formation which promotes gelation (Tsunenaga, M. et al., 1992. Connect. Tiss. Res. 28:113-123). The connective tissue homogenate and/or carrier may have excellent histocompatibility and elicit minimal antibody formation or immunological rejection, in certain embodiments. Keeping this in mind, the homogenized connective tissue may be made acellular, using methods known in the art, prior to homogenization, and methods of making such tissues acellular are described in U.S. Pat. Nos. 6,734,018 and 6,743,574; which are hereby incorporated by reference in their entirety.

An acellularization process used to prepare homogenized connective tissue of the present invention may be performed without damage to matrix and/or tissue structure, in some embodiments. Mechanical strength of a connective tissue may reside in the matrix structure of the tissue. The matrix structure may include collagens, hyaluronins, elastins, mucopolysaccharides and proteoglycans, among other components. An example of an acellularization method for use with soft tissues is described in U.S. Pat. Nos. 6,734,018 and 6,743,574, which are hereby incorporated by reference in their entirety. Connective tissue that is acellularized may have a thickness that does not exceed about 8 mm, about 6 mm, or about 4 mm, in certain embodiments. Acellularization processing may be altered to accommodate the thicker tissues.

Certain tissue repair compositions of the present invention may include elements in addition to the plurality of bone fragments and the carrier. Additional elements may be bioactive compounds, antibiotics (i.e., penicillin), antiviral agents (i.e., Triton X-100, Nonidet P-40, N-lauroyl sarcosinate, Brij-35, and peroxide generating agents), antitumor agents, analgesics, immunosuppressive agents (i.e., bovine intestinal alkaline phosphatase), permeation enhancers (i.e., fatty acid esters, such as the laurate, myristate and stearate monoesters of polyethylene glycol), nucleic acids, mesenchyrnal elements, gelation enhancing compounds (i.e., hyaluronic acid, chondroitin sulfate, dermatin sulfate, carboxymethylcellulose, methylcellulose, polyethylene glycol, or glycosamino glycans), or autogenously derived osteoblast cells, among others. Examples of bioactive compounds include: bone morphogenic proteins, transforming growth factor beta, fibroblast growth factor, insulin, vascular endothelial growth factor, and platelet derived growth factor, among others. In this respect, the invention includes other equivalent optional components readily known to those in the art. Tissue repair compositions of the present invention may include a calcium phosphate and/or calcium sulfate mineral component to produce an osteoinductive/osteoconductive composition which will harden prior to or post implantation. Tissue repair compositions of the present invention may also include particulate hydroxyapatite, calcium phosphate, magnesium phosphate, calcium carbonate, as extenders of the compositions and as sources of mineral in subsequent induced new bone formation.

In some embodiments, the tissue repair composition or components of a tissue repair composition, and optionally means for applying a tissue repair composition (i.e., syringe or spatula) to an implant site may be provided in a unitary kit. In other embodiments, the demineralized bone fragments and the connective tissue homogenate and/or the carrier may be prepared under sterile conditions and stored separately, or mixed and stored together, for later use. To facilitate clinical usage of described tissue repair compositions, the demineralized bone fragments and the carrier/connective tissue homogenate may be packaged separately in different forms and reconstituted and combined at the time of usage, in some embodiments. In other embodiments, the components may be combined to produce a tissue repair composition, which is then packaged, in a premixed format.

The premixed format provides the advantage of requiring minimal preparation by the individual clinician at the time of usage. In some embodiments, the tissue repair composition may be stored in an application means, such as a syringe, which will be used to apply the composition to an osseous defect site. The tissue repair composition may, for example, be stored in a 1 to 10 cc syringe that is capable of being coupled to a large gauge delivery tube/needle of appropriate length and inside diameter. In this regard, a delivery tube with an inside diameter of not less than 13 gauge is appropriate for the injection delivery into an implant site.

For on-site preparation, the carrier/homogenized connective tissue and demineralized bone may be provided in freeze-dried aliquots that are rehydrated just prior to being combined for use in clinical applications, in some embodiments. On-site preparation has the advantage of increasing the ability to vary the concentrations and quantities of the carrier/connective tissue homogenate and demineralized bone fragments used in preparation of the inventive tissue repair composition. Furthermore, on-site preparation permits the addition of optional components at the discretion of the clinician.

Certain embodiments of the present invention are directed to methods for the preparation of inventive tissue repair compositions, as described above. Such methods include combining a plurality of demineralized bone fragments and a carrier comprising a homogenized connective tissue. Certain inventive methods include combining demineralized bone fragments with a carrier such that the tissue repair composition produced between about 5 wt % and about 80 wt % or between about 30 wt % and about 50 wt % demineralized bone fragments. In some embodiments, the demineralized bone fragments and the carrier may be combined with at least one of the component, as described above. The methods may include packaging the inventive tissue repair compositions, in certain embodiments. In some embodiments, inventive methods of the present invention include providing at least one of bone tissue or bone tissue fragments and at least one connective tissue, and preparing demineralized bone fragments and homogenized connective tissue from the at least one bone tissue and the at least one connective tissue, as described above. Bone fragments may include at least one of bone particles and bone fibers from bone tissue. Some methods of preparing the tissue repair compositions of the present invention may include the production of particles or fibers from bone tissue, as discussed above. Bone fragments may be demineralized, as described above, in certain embodiments. The fragments may be demineralized to have less than about 8 wt % residual calcium, less than about 4 wt % residual calcium, or between about 0.5 wt % and about 4 wt % residual calcium, in some methods of the present invention. Certain methods of the present invention may include freeze-drying demineralized bone fragments. In some embodiments, the demineralized bone fragments may be freeze-dried to a point such that the freeze-dried fragments have an average residual moisture of less than about 10 wt %, or less than about 5 wt %. In some embodiments, freeze-dried demineralized bone fragments may be rehydrated before use in preparing the tissue repair compositions of the present invention. Rehydrated freeze-dried demineralized bone particles may have a residual moisture content of less than about 80 wt %, less than about 50 wt %, less than about 25 wt %, or between about 25 wt % and about 10 wt %, in certain embodiments.

Certain methods for producing the inventive tissue repair compositions may include preparing a connective tissue homogenate/carrier. Prior to homogenization, connective tissues (i.e., fascia, skin, tendons, ligaments, pericardium, and articular cartilage, among others) may be crudely fragmented. Connective tissue (e.g., fresh or freeze-dried) may be sliced, ground, carved, chipped, chopped, minced, cut, dissected, rent, ripped, sectioned, snipped, diced, shaved, comminuted, or trimmed into crude fragments. In some embodiments, the crude fragments may have an average diameter greater than about 50 microns. The crude fragments may be of varying sizes, in some embodiments. Essentially intact connective tissue or crude fragments of connective tissue (e.g., fresh or freeze-dried) may be homogenized at least one time to prepare the homogenate. The homogenization step(s) of certain inventive methods may involve shear-induced shredding of connective tissue. Connective tissue may be homogenized to have tissue fragments having an average diameter of less than about 50 microns, less than about 20 microns, or less than about 50 microns and more than about 5 microns. Water, at least one aqueous solution (e.g., isotonic saline) or other components may be combined with a connective tissue before homogenization.

Certain methods include at least one of (a) heating a connective tissue before it is homogenized, (b) heating a connective tissue while it is being homogenized, and (c) heating a connective tissue homogenate. In some embodiments the heating is done to a temperature of between about ambient temperature and about 100° C., or between about 37° C. and about 100° C. The heating may be carried out for between about 4 minutes and about 30 minutes. The heating may be accomplished using sonication, microwave irradiation, or conventional heat transfer from a heating component, among other methods known in the art.

In certain methods, the tissue repair composition may be cast in a mold. In some embodiments, a method may further include freeze-drying a cast composition or cross-linking a cast composition utilizing chemical reagents known in the art. Methods of the current invention may include sterilization of tissue repair compositions, components of tissue repair compositions, and/or sterilization of packaged tissue repair compositions/components. Sterilization may be performed using methods known in the art. The sterilization may involve the use of ionizing radiation, in some embodiments. In certain embodiments, the absorbed dose of ionizing radiation is between about 8.0 KGy and about 50 KGy, between about 8.0 KGy and about 25 KGy, and between about 8.0 KGy and about 18 KGy. In some embodiments, the sterilizing step includes placing the packaged composition on dry ice and irradiating the packaged composition. In certain embodiments, sterilization is performed at a temperature of between about –20° C. and –50° C. Certain methods of the present invention involve (a) providing at least one connective tissue and at least one bone tissue from at least one cadaver, (b) freeze-drying the connective tissue, (c) crudely fragmenting the connective tissue, (d) adding at least one of water, an aqueous solution (i.e., isotonic saline) or a water miscible polar organic solvent to the crude fragments to produce a mixture, which may optionally be heated, (e) homogenizing the mixture to produce a connective tissue homogenate, (f) fragmenting the bone tissue to produce fragments, (g) demineralizing the bone fragments, (h) freeze-drying the demineralized bone fragments, (i) selecting demineralized bone fragments having sizes within a particular range, (j) combining the selected demineralized bone fragments of the particular range with the connective tissue homogenate. Certain methods may include at least one of (a) heating a connective tissue before it is homogenized, (b) heating a connective tissue while it is being homogenized, (c) heating a connective tissue homogenate, and (d) heating the tissue repair composition. In some embodiments, heating is sufficient to reach a temperature of about 100° C. A microwave oven may be used in the heating step, in certain embodiments. Connective tissue homogenate may be heated and homogenized a second time before being combined with the demineralized bone fragments in certain methods of the present invention. In some embodiments, the selecting of bone fragments having sizes with a given range may involve the use of mesh sieves. In some embodiments, the tissue repair composition may be packaged, and the packaged composition may optionally be sterilized.

In certain embodiments, inventive tissue repair compositions of the present application may be applied to a prosthetic device utilized in neurological or orthopedic applications, to facilitate osteoconduction, and/or osteoinduction of native bone around the implant in order to build a stronger and more compatible association between the implant and the native bone. Implantable bone prostheses may include a substrate formed of a biocompatible metal, ceramic, mineral component, or composite; and at least a partial coating of tissue repair composition.

Certain embodiments of the present invention are directed to prosthetic devices comprising, an implantable prosthetic device, and a coating directly adjacent to at least a portion of a surface of the implantable prosthetic device. The coating includes at least one tissue repair composition comprising a plurality of demineralized bone fragments and a homogenized connective tissue.

Some embodiments of the present invention are directed to a method of coating a prosthetic device comprising, providing an implantable prosthetic device, and applying at least one tissue repair composition to at least a portion of a surface of the implantable prosthetic device. The tissue repair composition is as described above.

Further details of the process of the invention are presented in the examples that follow:

EXAMPLES

Example 1

Preparation of Tissue Repair Compositions Containing Freeze-Dried Fascia

Fascia lata and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and freeze-dried. The freeze-dried fascia was cut into small (about ½ cm by ½ cm) pieces (e.g., crude fragments). Isotonic saline in a volume (1 $cm^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

To prepare a first tissue repair composition, the sized, freeze-dried demineralized bone powder was added to the homogenized fascia until the final concentration of the bone was about 30% by weight. In a second tissue repair composition, the demineralized bone powder was added to the homogenized fascia until the final concentration of the bone was about 50% by weight. Samples of the tissue repair composition were sealed in sterilized glass vials in 2 g aliquots.

Example 2

Preparation of a Tissue Repair Composition Containing Freeze-Dried Tendon

Tendon and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and tendons were cleaned of unwanted tissues and freeze-dried. The freeze-dried tendon was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

In order to prepare the tissue repair composition, the freeze-dried demineralized bone powder was added to the heated, homogenized tendon tissue until the final concentration of the bone in the tissue repair composition was about 30% by weight. Samples were sealed in sterilized glass vials in 2 g aliquots.

Example 3

Preparation of Tissue Repair Compositions Containing Non-Freeze-Dried Fascia

Fascia and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and the bone was freeze-dried. Fresh, non-freeze-dried fascia was used. The fascia was cut into long strips and was mixed with water at a ratio of about 1:15 by weight. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

To prepare a first tissue repair composition, the demineralized bone powder was added to the homogenized, non-freeze-dried fascia until the final concentration of the bone was about 30% by weight. In a second tissue repair composition, the demineralized bone powder was added to a final concentration of about 50% by weight. Samples of the tissue repair compositions were sealed in sterilized glass vials in 2 g aliquots.

Example 4

Preparation of a Tissue Repair Composition Containing Rehydrated Freeze-Dried Fascia and Rehydrated Freeze-Dried Bone Fascia and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and freeze-dried. The fascia was rehydrated prior to being used in making of the composition. The rehydrated fascia was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

The ground demineralized bone powder was prepared by impact fragmentation, followed by freeze-drying, and finally the particles were sized using mesh sieves. Ground demineralized bone particles having a size in the range of about 125 to 500 microns were used.

The freeze-dried demineralized bone particles were rehydrated prior to being combined with the homogenized fascia. The final concentration of the rehydrated bone particles in the tissue repair composition was about 20 wt %. The resulting tissue repair composition was a gel. The gel was packaged in 5 mL Luerlock syringes. The gel was easily extruded from the syringe. A thirteen-gauge needle was attached to the syringe, and the gel was easily extruded through the needle, as well.

Example 5

Preparation of a Molded Tissue Repair Composition Containing Freeze-Dried Fascia Fascia and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and freeze-dried. The freeze-dried fascia was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 125 to 710 microns and demineralized to an average weight percent residual calcium of 2±1% were used.

In order to prepare the tissue repair composition, the freeze-dried demineralized bone powder was added to the homogenized fascia until the final concentration of the bone in the composition was about 40% by weight. The tissue repair composition was then placed into different containers and molds, and freeze-dried using a two-day cycle as prescribed by the manufacturer of the freeze-drier. The freeze-dried, molded, tissue repair compositions demonstrated high mechanical strength and maintained the shape of their mold. The cast tissue repair composition may be rehydrated using an isotonic solution to make it malleable or may be cross-linked with a fixative such as glutaraldehyde, EDC, or genapin to help retain its solid, rigid, molded form to be used in applications where a specific shape and mechanical strength would be desirable.

Example 6

Preparation of Tissue Repair Compositions Containing Freeze-Dried Fascia

Fascia and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products. The bone and fascia were cleaned of unwanted tissues and freeze-dried.

Ground demineralized bone powder was prepared by impact fragmentation of bone, followed by freeze-drying. The freeze-dried particles were sized using mesh sieves. Ground demineralized bone particles having a size in the range of about 125 to 500 microns and demineralized to an average weight percent residual calcium of 2±1% were used.

The small pieces of connective tissue and the saline solution were brought to a temperature of 100° C. using a heating plate and the mixture was heated at this temperature for an additional 5 minutes. Water was added to the mixture to replace the solution lost due to evaporation. The mixture was transferred into a conventional blender and mechanically homogenized at approximately 15,000 rpm (maximum shear speed of the commercially available blender) for 5 minutes. The mixture was again heated to a temperature of 100° C. using the heating plate, and maintained at this temperature for an additional 5 minutes. The heated mixture was again blended for two, 2-minute pulses to produce the homogenized fascia.

To prepare a first tissue repair composition, the sized, freeze-dried demineralized bone powder was added to the homogenized fascia until the final concentration of the bone was about 30% by weight. In a second tissue repair composition, the demineralized bone powder was added to the homogenized fascia until the final concentration of the bone was about 50% by weight.

Example 7

Preparation of Tissue Repair Compositions Containing Freeze-Dried Fascia

Fascia and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and freeze-dried. The freeze-dried fascia was cut into small, ½ cm by ½ cm pieces (e.g., crude fragments). Isotonic saline in a volume (1 cm$^3$ of isotonic saline corresponds to about 1 g) approximating 50 times the weight of the tissue to be processed was added to cut fascia. The fascia and saline were brought to a temperature of 100° C. using a heating plate and was heated at this temperature for an additional 5 minutes. Water was added to replace the solution lost due to evaporation. The heated material was transferred into a blender and mechanically modified at 15,000 rpm (maximum shear speed of the commercially available blender) for 5 minutes. The homogenized connective tissue was again heated to a temperature of 100° C. using the heating plate, and maintained at this temperature for an additional 5 minutes. The heated homogenate was blended for two, 2-minute pulses. The material was divided and placed into centrifuge containers and spun at 1000 rcf for 5, 7, 9, and 10 minutes, respectively. Water in the material separated into a distinct layer after the centrifugation process. The volume of the water layer was proportional to the centrifugation time. The materials remaining after removal of the water layer had different consistencies. To prepare tissue repair compositions, the sized, freeze-dried demineralized bone powder was added to the various homogenized materials until the final concentration of the bone was about 30% by weight. The viscosities of the tissue repair compositions correlated to the differing consistencies of the homogenized connective tissue materials used in their preparation.

Example 8

Determination of New Bone Formation

Fascia lata and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and freeze-dried. The freeze-dried fascia was cut into small (about ½ cm by ½ cm) pieces (e.g., crude fragments). Isotonic saline in a volume (1 cm$^3$ of isotonic saline corresponds to about 1 g) approximating 20 times the weight of tissue, was added to a container containing the cut fascia. The ingredients were heated to a temperature of 100° C. using a microwave oven, and maintained at this temperature for 4 minutes. Water was added to the heated composition to replace the liquid lost to evaporation. The heated composition was transferred into a conventional blender and mechanically homogenized (e.g., blended) for 5 minutes. The homogenized connective tissue was re-heated for an additional 4 minutes in the microwave oven, and mechanical homogenization was repeated for an additional 5 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

Tissue repair compositions having a putty-like consistency were prepared by adding the sized, freeze-dried demineralized bone powder to the homogenized fascia until the final concentration of the bone was about 24%, 26%, 30%, and 50% by weight, respectively.

The prepared tissue repair compositions, a demineralized bone matrix (DBM) control (without homogenized connective tissue), and a homogenized tissue sample without DBM were implanted heterotopically (e.g., into muscle pouches) in the hind quarters of athymic (e.g., nude) mice. Each implant (other than the homogenized tissue-only sample) contained 20 mg of demineralized bone matrix. The amounts of materials implanted were varied to always implant 20 mg of DBM i.e., 40 mg of the 50% DBM composition was implanted. In that the DBM constituted 50% by weight, and the homogenized connective tissue constituted 50% by weight, the total implant of 40 mg contained 20 mg of DBM. Thus, 85 mg, 77 mg, 68 mg, and 40 mg of the 24 wt %, 26 wt %, 30 wt %, and 50 wt % tissue repair compositions were implanted, respectively. Three mice with two implants per mouse were used for each of the four tissue repair compositions, the DBM control, and the homogenized tissue-only sample (e.g., 18 mice in all and 36 implants).

After 28 days, the implants were explanted, and one explant from each mouse was fixed. At least one histological section was cut from the center of each of these explants. Samples were fixed in 10% buffered formalin. Standard dehydration, embedding and sectioning protocols were used to produce light microscopy slides that were subsequently stained with hematoxylin and eosin. Using histomorphometric analysis, the percent new bone formed was calculated as a cross-sectional area of newly formed bone ($mm^2$) divided by the total cross-sectional area ($mm^2$) for a representative microscopic view of a histology slide multiplied by 100. Every other field of view with at least 50% bone content was used as a representative view with about 10 representative views being analyzed per slide.

The demineralized bone that was implanted without homogenized connective tissue (e.g., the control) produced about 9.6% new bone growth, and the homogenized fascia alone (freeze dried material) produced about 3.8% new bone growth. The 24%, 26%, 30%, 50% demineralized bone to homogenized connective tissue compositions resulted in about 6.4%, 11.1%, 14.5%, and 16.2% new bone growth, respectively.

Other Embodiments

It is to be understood that while the invention has been described in conjunction with the detailed description thereof, the foregoing description is intended to illustrate and not limit the scope of the invention. Other aspects, advantages, and modifications are within the scope of the following claims.

What is claimed is:

1. A method for preparing a tissue repair composition comprising, combining a plurality of demineralized bone fragments and a carrier, wherein the carrier comprises homogenized connective tissue.

2. The method of claim 1, wherein the plurality of demineralized bone fragments and the homogenized connective tissue are prepared from bone and connective tissue obtained from a single cadaver source.

3. The method of claim 1, further comprising providing at least one bone tissue and at least one connective tissue from a single cadaver source, and preparing demineralized bone fragments and homogenized connective tissue from the at least one bone tissue and the at least one connective tissue.

4. The method of claim 1, further comprising providing a plurality of bone fragments, and demineralizing the bone fragments to produce demineralized bone fragments.

5. The method of claim 1, further comprising providing at least one bone tissue, preparing at least one of bone particles and bone fibers from the bone tissue, and demineralizing the bone particles or the bone fibers to produce demineralized bone fragments.

6. The method of claim 1, further comprising providing at least one cortical bone tissue, and preparing the plurality of demineralized bone fragments from the at least one cortical bone tissue.

7. The method of claim 1, wherein the plurality of demineralized bone fragments comprises demineralized cortical bone particles.

8. The method of claim 1, further comprising providing at least one cancellous bone tissue, and preparing the plurality of demineralized bone fragments from the at least one cancellous bone tissue.

9. The method of claim 1, wherein the plurality of demineralized bone fragments comprises demineralized cancellous bone particles.

10. The method of claim 1, wherein the plurality of demineralized bone fragments comprises at least one of demineralized bone particles and demineralized bone fibers.

11. The method of claim 10, wherein the composition comprises demineralized bone fibers having an average thickness of between about 0.1 mm and about 0.3 mm and an average width of between about 0.3 mm and about 1.0 mm.

12. The method of claim 10, wherein the demineralized bone particles have an average particle diameter of between about 125 microns and about 4 mm.

13. The method of claim 10, wherein the demineralized bone particles have an average particle diameter of between about 125 microns and about 500 microns.

14. The method of claim 10, wherein the demineralized bone particles have an average particle diameter of between about 125 microns and about 850 microns.

15. The method of claim 10, wherein the demineralized bone particles have an average particle diameter of between about 250 microns and about 710 microns.

16. The method of claim 1, wherein the plurality of demineralized bone fragments comprises at least one of demineralized allogenic cortical bone and demineralized xenogenic cortical bone.

17. The method of claim 1, further comprising providing a cortical bone tissue, and preparing demineralized bone fragments from the cortical bone tissue, wherein the cortical bone tissue is an allogenic tissue or a xenogenic tissue.

18. The method of claim 1, wherein the composition comprises between about 5 wt % and about 80 wt % demineralized bone fragments.

19. The method of claim 1, wherein the composition comprises between about 30 wt % and about 50 wt % demineralized bone fragments.

20. The method of claim 1, wherein the demineralized bone fragments have less than about 8 wt % residual calcium.

21. The method of claim 1, wherein the demineralized bone fragments have less than about 4 wt % residual calcium.

22. The method of claim 1, wherein the demineralized bone fragments have between about 0.5 wt % and about 4 wt % residual calcium.

23. The method of claim 1, wherein the carrier comprises at least one of homogenized fascia, homogenized tendons, homogenized ligaments, homogenized pericardium, and homogenized articular cartilage.

24. The method of claim 1, wherein the homogenized connective tissue is prepared by a homogenization method resulting in shear-induced shredding of connective tissue.

25. The method of claim 1, wherein the homogenized connective tissue is prepared by a method comprising at least one of (a) heating a connective tissue before it is homogenized, (b) heating a connective tissue while it is being homogenized, and (c) heating a connective tissue homogenate.

26. The method of claim 25, wherein the heating is at a temperature between about ambient temperature and about 100° C.

27. The method of claim 26, wherein the temperature is between about 37°C. and about 100° C.

28. The method of claim 25, wherein the heating is accomplished using sonication, microwave irradiation, or conventional heat transfer from a heating component.

29. The method of claim 25, wherein the heating is carried out for between about 4 minutes and about 30 minutes.

30. The method of claim 1, wherein the composition is a gel, a paste, or a putty.

31. The method of claim 1, wherein the composition has a viscosity such that the composition can be extruded through at least a 13 gauge or larger gauge syringe needle.

32. The method of claim 1, further comprising casting the composition in a mold.

33. The method of claim 32, further comprising freeze-drying the cast composition.

34. The method of claim 1, wherein the composition is sterile.

35. The method of claim 1, further comprising placing the composition in a package.

36. The method of claim 35, further comprising sterilizing the packaged composition.

37. The method of claim 36, wherein the sterilizing step further comprises treating the packaged composition with ionizing radiation.

38. The method of claim 37, wherein the absorbed dose of ionizing radiation is between about 8.0 KGy and about 50 KGy.

39. The method of claim 37, wherein the absorbed dose of ionizing radiation is between about 8.0 KGy and about 25 KGy.

40. The method of claim 37, wherein the absorbed dose of ionizing radiation is between about 8.0 KGy and about 18 KGy.

41. The method of claim 36, wherein the sterilizing step further comprises placing the packaged composition on dry ice and irradiating the packaged composition.

42. The method of claim 36, wherein the packaged composition is sterilized at a temperature of between about −20° C. and −50° C.

43. The method of claim 1, wherein the plurality of demineralized bone fragments comprises freeze-dried demineralized bone particles.

44. The method of claim 1, wherein the plurality of demineralized bone fragments comprises freeze-dried demineralized bone fragments having an average residual moisture of less than about 10 wt %.

45. The method of claim 1, wherein the plurality of demineralized bone fragments comprises freeze-dried demineralized bone particles having an average residual moisture of less than about 5 wt %.

46. The method of claim 1, wherein the plurality of demineralized bone fragments comprises freeze-dried demineralized bone fragments that have been rehydrated.

47. The method of claim 46, wherein the plurality of demineralized bone fragments comprises rehydrated freeze-dried demineralized bone fragments having a residual moisture content of less than about 80 wt %.

48. The method of claim 46, wherein the plurality of demineralized bone fragments comprises rehydrated freeze-dried demineralized bone fragments having a residual moisture content of less than about 50 wt %.

49. The method of claim 46, wherein the plurality of demineralized bone fragments comprises rehydrated freeze-dried demineralized bone fragments having a residual moisture content of less than about 25 wt %.

50. The method of claim 46, wherein the plurality of demineralized bone fragments comprises rehydrated freeze-dried demineralized bone fragments having a residual moisture content of between about 10 wt % and about 25 wt %.

51. The method of claim 1, wherein the combining is done with a blender.

52. The method of claim 1, wherein the homogenized connective tissue is prepared comprising,
  obtaining at least one connective tissue from at least one cadaver;
  freeze-drying the connective tissue;
  crudely fragmenting the connective tissue;
  adding at least one of water, an aqueous solution, or a water miscible polar organic solvent to the crude fragments to produce a mixture; and
  homogenizing the mixture to produce homogenized connective tissue.

53. The method of claim 52, further comprising heating the water, aqueous solution, or solvent with the crude fragments.

54. The method of claim 52, wherein the demineralized bone fragments are prepared comprising,
  obtaining at least one bone tissue from at least one cadaver;
  fragmenting the bone tissue;
  demineralizing the bone fragments;
  freeze-drying the demineralized bone fragments; and
  selecting demineralized bone fragments of a particular range for combining with the homogenized connective tissue.

55. The method of claim 54, further comprising heating the tissue repair composition.

56. The method of claim 54, wherein sieves are employed for the selecting.

57. The method of claim 54, wherein the selected demineralized bone fragments have an average diameter of between about 250 and about 710 microns.

58. The method of claim 54, wherein the composition comprises between about 5 wt % and about 80 wt % of the selected demineralized bone fragments.

59. A tissue repair composition prepared by the method of claim 54.

60. The method of claim 52, wherein the connective tissue is fascia.

61. The method of claim 52, wherein the connective tissue and the bone tissue are obtained from a single cadaver.

62. The method of claim 52, wherein the aqueous solution comprises isotonic saline.

63. The method of claim 52, wherein the connective tissue homogenate is heated.

64. The method of claim 52, wherein a blender is employed for the homogenizing.

65. The method of claim 52, wherein the mixture is heated to a temperature of about 100° C.

66. The method of claim 65, wherein a microwave oven is used for the heating.

67. The method of claim 66, wherein the connective tissue homogenate is heated and homogenized a second time before being combined with the demineralized bone fragments.

68. The method of claim 1, wherein the demineralized bone fragments are prepared comprising,
obtaining at least one bone tissue from at least one cadaver;
fragmenting the bone tissue;
demineralizing the bone fragments;
freeze-drying the demineralized bone fragments; and
selecting demineralized bone fragments of a particular range for combining with the homogenized connective tissue.

69. The method of claim 1, further comprising packaging the tissue repair composition.

70. The method of claim 69, further comprising sterilizing the packaged tissue repair composition.

71. The method of claim 1, wherein the tissue repair composition further comprises a bioactive compound.

72. The method of claim 71, wherein the bioactive compound is a growth factor.

73. The method of claim 71, wherein the growth factor is a transforming growth factor beta, a fibroblast growth factor, a vascular endothelial growth factor, or a platelet derived growth factor.

74. The method of claim 71, wherein the bioactive compound is a bone morphogenic protein or insulin.

75. A tissue repair composition prepared by a method comprising, combining a plurality of demineralized bone fragments and a carrier, wherein the carrier comprises homogenized connective tissue.

* * * * *

UNITED STATES PATENT AND TRADEMARK OFFICE
CERTIFICATE OF CORRECTION

| | | |
|---|---|---|
| PATENT NO. | : 7,498,040 B2 | Page 1 of 1 |
| APPLICATION NO. | : 11/247229 | |
| DATED | : March 3, 2009 | |
| INVENTOR(S) | : Masinaei et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 233 days.

Signed and Sealed this
Seventeenth Day of July, 2012

David J. Kappos
*Director of the United States Patent and Trademark Office*